United States Patent [19]

Cocola et al.

[11] 4,079,622
[45] Mar. 21, 1978

[54] APPARATUS FOR DETERMINING THE SMOKE DENSITY OF FLUE GASES OF GAS AND FUEL OIL

[75] Inventors: Raul Cocola, San Donato Milanese; Leandro Borgacci, Milan; Arnaldo Gambini, San Donato Milanese, all of Italy

[73] Assignee: Snamprogetti S.p.A., Italy

[21] Appl. No.: 722,140

[22] Filed: Sep. 10, 1976

Related U.S. Application Data

[63] Continuation of Ser. No. 579,705, May 21, 1975, abandoned.

[51] Int. Cl.$^2$ .................. G01N 1/24; G01N 15/06
[52] U.S. Cl. ............................ 73/28; 73/421.5 A
[58] Field of Search ............ 73/28, 421.5 R, 421.5 A; 23/254 R; 55/267, 270; 256/38

[56] References Cited

U.S. PATENT DOCUMENTS

| | | | |
|---|---|---|---|
| 1,100,171 | 6/1974 | Brown | 73/421.5 R |
| 1,321,062 | 11/1919 | Lamb | 23/254 R |
| 2,129,527 | 9/1938 | Fassin | 73/28 |
| 3,166,938 | 1/1965 | Weyauch et al. | 23/254 R |
| 3,286,506 | 11/1966 | Lloyd | 23/254 R |
| 3,304,783 | 2/1967 | Quigley | 73/421.5 R |
| 3,841,145 | 10/1974 | Boubel | 73/28 |
| 3,892,547 | 7/1975 | Lyshkow | 73/421.5 R |

*Primary Examiner*—S. Clement Swisher
*Attorney, Agent, or Firm*—Morgan, Finnegan, Pine, Foley & Lee

[57] ABSTRACT

Apparatus for determining the smoke density of flue gas by providing substantially uniform smoke spots, which includes a piston-actuated pump for withdrawing gas from a smokestack through a cooled probe so that cooled gas from the stack is drawn through filter paper and is then cooled further for the removal of condensate. The cooled, dried gas then flows from the system during the compression stroke of the piston of the suction pump through a by-pass provided with a one-way value. The present invention provides the uniformity required to facilitate optical comparison between the obtained spots in the described filter paper and standard reference spots.

1 Claim, 4 Drawing Figures

APPARATUS FOR DETERMINING THE SMOKE DENSITY OF FLUE GASES OF GAS AND FUEL OIL

This is a continuation of application Ser. No. 579,705 filed May 21, 1975, now abandoned.

The present invention relates to an apparatus for determining the smoke density of flue gases.

Generally the determination of the smoke density is carried out by separating the unburned solids from a known volume of flue gas by filtering it through paper or the like. Such separated amount is then evaluated by visual comparison with a set of spots having a grey tonality running from white to black, an increasing smoke density corresponding thereto. Such a comparison gives an indication generally accepted both as to the completeness of the combustion reaction and to the degree of the comburent/combustible mixing as a function of the air/fuel ratio. Accordingly, several devices suitable for the determination of such a density are known.

These devices present, however, more or less noticeable drawbacks, among which may be mentioned the following: unsatisfactory uniformity of the soot spot, remarkable deterioration of some parts thereof and poor reproducibility of the tests.

The apparatus of the present invention for determining smoke density aims to improve the uniformity of the soot spot.

A further object of the present invention is the improvement of the accuracy and reproducibility of the determinations relating to distillates in general and in particular of those relating to fuel oils having viscosities up to about 18 Engler at 50° C.

The main feature of the present invention is the filtering through a paper, at a temperature remarkably lower than the operating temperature kept constant by water cooling or the like, optimized by a suitable choice of the diameter of the sampling probe and of the value of the depression in the suction phase.

Further features and characteristics of the present invention will be shown by the following specification and accompanying drawings given by may of example.

The apparatus which is the subject of the present invention is comprised of the following elements:
a. sampling probe, suitably cooled and arranged orthogonal to the flue gas glow;
b. tight clamping system for the filter paper;
c. cooling-drying system for sampled gases;
d. electric exhaust valve for filtered gases and
e. suction syringe.

Figure 1:
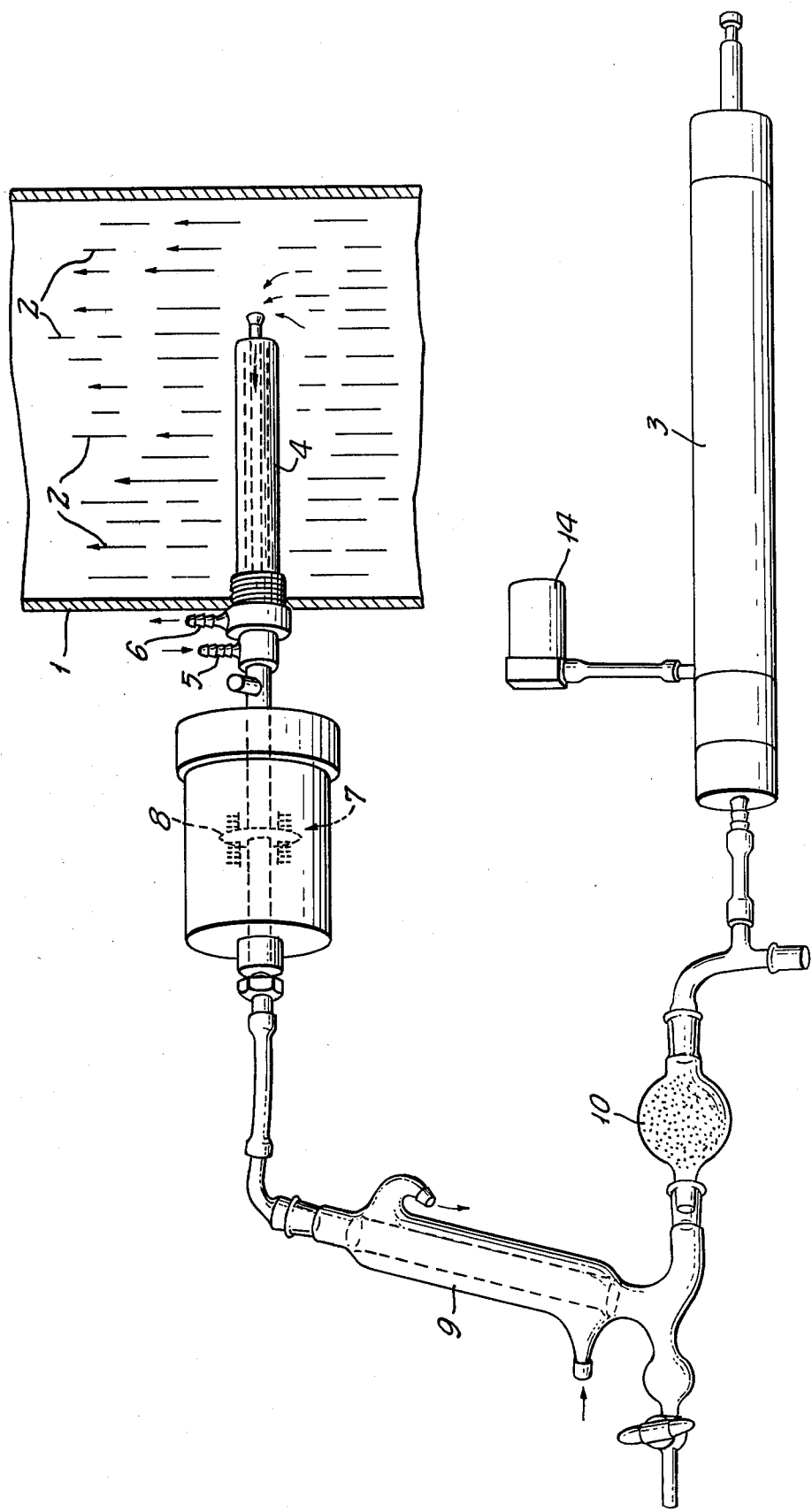
FIG. 1 is an elevation of the apparatus of the invention.
Figure 2:
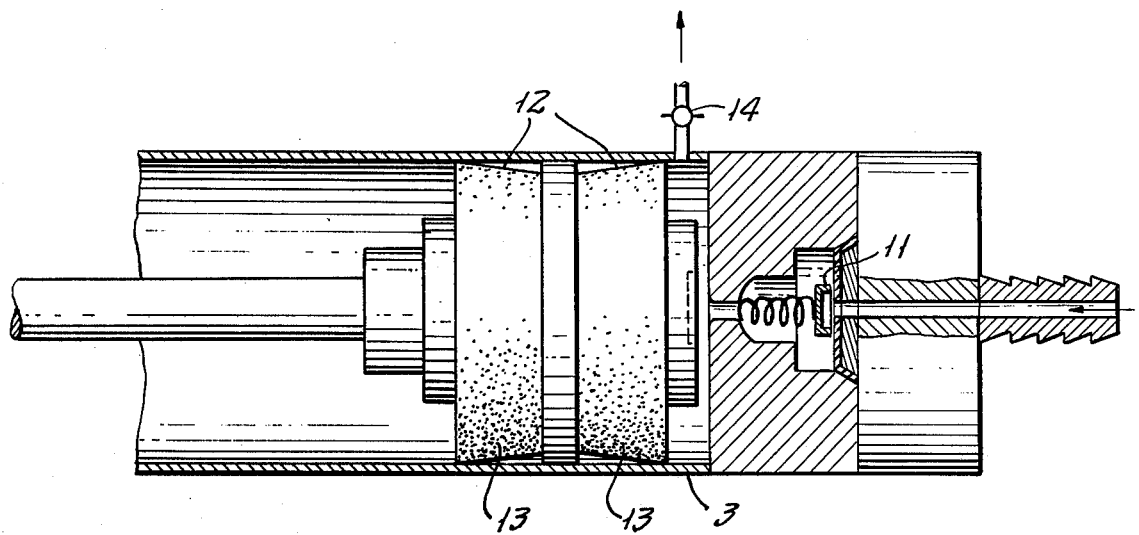
FIG. 2 is a longitudinal section of the suction syringe.
Figure 3:
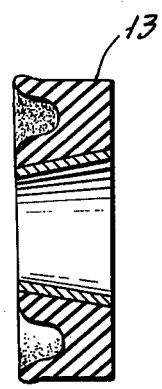
FIG. 3 is a detail of one of the two elements sealing the piston of the syringe of FIG. 2.

The apparatus which is the subject of the present invention will be described with reference to its operation. Flue gas 2, at a known temperature, coming from the lower part of a smokestack 1 is withdrawn by syringe 3 through probe 4 having an appropriate diameter and provided with a cooling jacket, having inlet 5 and outlet 6 for the circulation of a cooling fluid such as water or air. Flue gas 2 reaches, through probe 4, tight filtering system 7 provided with filter paper 8.

Flue gas 2, having passed through filter paper 8, passes through cooler 9 where it is suitably cooled to eliminate the most of the condensate. Drier 10, preferably of spherical shape, contains silica gel for retaining the reminder of the condensate and including an indicator for signalling, by its colour change, the exhaustion thereof.

This group 9 – 10 prevents the recycle of acid substances capable of producing remarkable modifications of the materials constituting the apparatus.

Flue gas 2, thus cooled and dried, reaches syringe 3, passing through a non-return valve 11, and fills the volume of syringe 3 made available by piston 12 in the extreme suction position.

The head of piston 12 includes two symmetrical elements 13 having a flanged edge for improving the sealing of syringe 3.

A predetermined number of strokes is employed for each soot spot.

In the compression phase of piston 12 the flue gas is evacuated from the circuit through a valve 14 in a by-pass connected to said pump. The flue gas is thus prevented from flowing in an opposite direction so as to avoid the detachment of the soot from filter paper 8.

Figure 4:
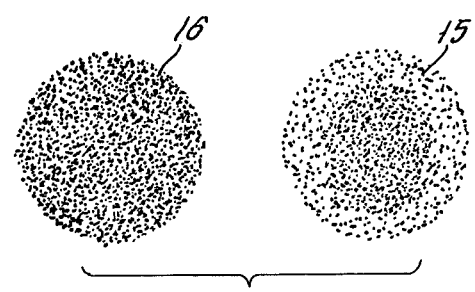
FIG. 4 is a comparative illustration of soot spots made with the apparatus of the invention and with prior art apparatus.

Finally, FIG. 4 shows two soot spots 15 and 16. One, numbered 15, was obtained with prior art apparatus. The other, numbered 16, was obtained with the same apparatus in combination with a cooled probe, a cooler-drier group and a double seal piston head according to the present invention.

Comparing soot spots 15 and 16 of FIG. 4 it is possible to notice clearly the different distribution of the soot particles. 15 presents clearly a higher concentration in the central zone. 16, obtained with the apparatus according to the invention, presents, on the contrary, uniform distribution of the particles on the whole impact zone. 16 makes possible, therefore, an evaluation, e.g. an optical one, which is more reliable, quicker and more accurate.

It has been found that, by a suitable choice of the size parameters and running conditions, the smoke densities given by the apparatus which is the subject of the invention correspond with the ones obtained according to ASTM rules.

What we claim is:

1. Apparatus for determining the smoke density of flue gas by providing substantially uniform smoke spots on filter paper which comprises the combination, with a smokestack, of a probe having its inner and extending orthogonally into the smokestack, a cooling jacket surrounding the outer end of said probe and having an inlet and an outlet for the circulation of cooling fluid, a piston-actuated suction pump, a gas passageway connecting the pump with the probe, an enclosed filter having means for holding filter paper transversely across said passageway adjacent the outer end of said probe and upon which is deposited a substantially uniform smoke spot to facilitate optical comparison between said spot and standard spots used for purposes of comparison, cooling means surrounding said passageway between said filter and said pump, a drier extending across said passageway between the cooling means and the pump, and a one-way valve associated with said pump and adapted to permit gas to flow from the pump during the compression stroke of said piston.

* * * * *